(12) United States Patent
Chervitz et al.

(10) Patent No.: US 7,758,581 B2
(45) Date of Patent: Jul. 20, 2010

(54) POLYAXIAL REAMING APPARATUS AND METHOD

(75) Inventors: Alan Chervitz, Palm Harbor, FL (US); Daniel J. Triplett, Providence, UT (US)

(73) Assignee: Facet Solutions, Inc., Hopkinton, MA (US)

( * ) Notice: Subject to any disclaimer, the term of this patent is extended or adjusted under 35 U.S.C. 154(b) by 934 days.

(21) Appl. No.: 11/388,389

(22) Filed: Mar. 24, 2006

(65) Prior Publication Data

US 2006/0217728 A1 Sep. 28, 2006

Related U.S. Application Data

(60) Provisional application No. 60/666,209, filed on Mar. 28, 2005.

(51) Int. Cl.
*A61B 17/00* (2006.01)
*A61B 17/17* (2006.01)
*A61B 17/58* (2006.01)
*A61B 17/60* (2006.01)

(52) U.S. Cl. .................. 606/80; 606/79; 606/86 R; 606/96

(58) Field of Classification Search ............. 606/79–91, 606/61, 67, 916
See application file for complete search history.

(56) References Cited

U.S. PATENT DOCUMENTS

| | | | |
|---|---|---|---|
| 4,743,260 A | 5/1988 | Burton | |
| 5,092,866 A | 3/1992 | Breard et al. | |
| 5,180,393 A | 1/1993 | Commarmond | |
| 5,282,863 A | 2/1994 | Burton | |
| 5,375,823 A | 12/1994 | Navas | |
| 5,415,661 A | 5/1995 | Holmes | |
| 5,456,722 A | 10/1995 | Mcleod et al. | |
| 5,480,401 A | 1/1996 | Navas | |
| 5,496,318 A | 3/1996 | Howland et al. | |
| 5,540,688 A | 7/1996 | Navas | |
| 5,562,737 A | 10/1996 | Graf | |
| 5,609,634 A | 3/1997 | Voydeville | |
| 5,645,545 A * | 7/1997 | Bryant | ......................... 606/62 |

(Continued)

FOREIGN PATENT DOCUMENTS

EP 322334 B1 2/1992

(Continued)

*Primary Examiner*—Thomas C Barrett
*Assistant Examiner*—Sameh Boles
(74) *Attorney, Agent, or Firm*—Peter K. Johnson; G. Jo Hays; Barbara Daniels

(57) ABSTRACT

A reamer may be designed to engage a guide member, such as a guide wire, implanted in bone at any of a plurality of relative orientations such that the resulting resection of the bone does not depend on the relative orientation. The reamer may have a shaft that receives torque and a reaming head with a cavity into which a protruding portion of the guide wire is insertable. The cavity may have a generally conical shape capable of receiving the guide wire at a variety of relative orientations. The orientation of the reaming head is determined not by that of the guide wire, but by a stationary frame to which the reamer is coupled. The reamer may optionally have an offset assembly that causes the reaming head to rotate about an axis displaced from that of the shaft to reduce the size of the incision required to reaming head.

20 Claims, 7 Drawing Sheets

U.S. PATENT DOCUMENTS

| | | |
|---|---|---|
| 5,645,599 A | 7/1997 | Samani |
| 5,672,175 A | 9/1997 | Martin |
| 5,725,582 A | 3/1998 | Bevan et al. |
| 5,749,873 A | 5/1998 | Fairley |
| 5,836,948 A | 11/1998 | Zucherman et al. |
| 5,860,977 A | 1/1999 | Zucherman et al. |
| 5,876,404 A | 3/1999 | Zucherman et al. |
| RE36,221 E | 6/1999 | Breard et al. |
| 5,961,516 A | 10/1999 | Graf |
| 5,986,169 A | 11/1999 | Gjunter |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,102,915 A * | 8/2000 | Bresler et al. ............ 606/80 |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,241,730 B1 | 6/2001 | Alby |
| 6,267,764 B1 | 7/2001 | Elberg |
| 6,280,444 B1 | 8/2001 | Zucherman et al. |
| 6,290,700 B1 | 9/2001 | Schmotzer |
| 6,293,949 B1 | 9/2001 | Justis et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,471,704 B2 | 10/2002 | Gertzbein et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,585,769 B1 | 7/2003 | Muhanna et al. |
| 6,616,669 B2 | 9/2003 | Ogilvie et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,652,585 B2 | 11/2003 | Lange |
| 6,676,706 B1 * | 1/2004 | Mears et al. ............ 623/22.4 |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,733,534 B2 | 5/2004 | Sherman |
| 6,761,719 B2 | 7/2004 | Justis et al. |
| 6,761,720 B1 | 7/2004 | Senegas |
| 6,783,527 B2 | 8/2004 | Drewry et al. |
| 6,796,983 B1 | 9/2004 | Zucherman et al. |
| 6,835,205 B2 | 12/2004 | Atkinson et al. |
| 6,835,207 B2 | 12/2004 | Zacouto et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0091446 A1 | 7/2002 | Zucherman et al. |
| 2002/0116000 A1 | 8/2002 | Zucherman et al. |
| 2002/0143331 A1 | 10/2002 | Zucherman et al. |
| 2002/0183746 A1 | 12/2002 | Zucherman et al. |
| 2003/0009226 A1 | 1/2003 | Graf |
| 2003/0065330 A1 | 4/2003 | Zucherman et al. |
| 2003/0109880 A1 | 6/2003 | Shirado et al. |
| 2003/0191470 A1 | 10/2003 | Ritland |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0143264 A1 | 7/2004 | Mcafee |
| 2004/0147928 A1 | 7/2004 | Landry et al. |
| 2004/0152955 A1 * | 8/2004 | McGinley et al. ......... 600/300 |
| 2004/0153071 A1 | 8/2004 | Zucherman et al. |
| 2004/0153080 A1 * | 8/2004 | Dong et al. ............. 606/80 |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0220568 A1 | 11/2004 | Zucherman et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0033434 A1 | 2/2005 | Berry |
| 2005/0033439 A1 | 2/2005 | Gordon et al. |
| 2005/0043797 A1 | 2/2005 | Lee |
| 2005/0113927 A1 | 5/2005 | Malek |
| 2005/0177172 A1 * | 8/2005 | Acker et al. ............ 606/99 |
| 2005/0273167 A1 * | 12/2005 | Triplett et al. ........ 623/17.11 |

FOREIGN PATENT DOCUMENTS

| | | |
|---|---|---|
| EP | JP10277070 A2 | 10/1998 |
| EP | 768843 B1 | 2/1999 |
| EP | 669109 B1 | 5/1999 |
| EP | 1299042 A2 | 4/2003 |
| EP | 1303224 A1 | 4/2003 |
| EP | 1303225 A1 | 4/2003 |
| EP | 1414358 A2 | 5/2004 |
| EP | 1448109 A2 | 8/2004 |
| EP | 1239785 B1 | 9/2004 |
| EP | 1343424 B1 | 9/2004 |
| EP | 1399078 B1 | 12/2004 |
| WO | WO9421185 A1 | 9/1994 |
| WO | WO9822033 A1 | 5/1998 |
| WO | WO9921500 A1 | 5/1999 |
| WO | WO9921501 A1 | 5/1999 |
| WO | WO0145576 A1 | 6/2001 |
| WO | WO0156489 A1 | 8/2001 |
| WO | WO0164144 A2 | 9/2001 |
| WO | WO0191657 A1 | 12/2001 |
| WO | WO0191658 A1 | 12/2001 |
| WO | WO0203882 A2 | 1/2002 |
| WO | WO0207623 A1 | 1/2002 |
| WO | WO0230336 A2 | 4/2002 |
| WO | WO02067792 A2 | 9/2002 |
| WO | WO02067793 A2 | 9/2002 |
| WO | WO02102259 A2 | 12/2002 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004039239 A2 | 5/2004 |

| WO | WO2004039243 A2 | 5/2004 |
| WO | WO2004041066 A2 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |

* cited by examiner

POLYAXIAL REAMING APPARATUS AND METHOD

CROSS-REFERENCE TO RELATED APPLICATIONS

This application claims the benefit of the following:

U.S. Provisional Patent Application Ser. No. 60/666,209 filed Mar. 28, 2005 entitled POLYAXIAL REAMING APPARATUS AND METHOD.

BACKGROUND OF THE INVENTION

1. The Field of the Invention

The present invention relates to implantable medical devices and methods, and more precisely, to systems and methods for preparing a bone surface to receive an implant.

2. The Relevant Technology

Orthopedic medicine provides a wide array of implants that can be attached to bone to alleviate various pathologies. One unique challenge in the use of implants secured to bone, such as orthopedic implants, is the preparation of the bone surface to receive the implant. In order to provide secure fixation of the implant to the bone, the bone surface must typically be shaped in a manner that closely matches the shape of the adjacent implant surface. This may require any of several resection processes including boring, reaming, rasping, milling, and the like.

Certain bone shaping procedures are facilitated through the use of implanted guide members such as guide wires. For example, a guide wire may be placed in a pedicle of a vertebra prior to reaming or insertion of a pedicle screw to guide the reaming or screw implantation procedure. The orientation of the guide member often determines the orientation of the resulting resection surface or pedicle screw. Unfortunately, it may be difficult to implant a guide wire at a precise angle with respect to the vertebra. Furthermore, many surgeons have their own preferred methods of implanting guide wires, and such methods often are not designed to implant the guide wire at any specific angle relative to the bone.

Additionally, a fixation member such a pedicle screw will often be implanted along the axis of the guide member. Accordingly, the fixation member and the resection often are required to have the same axis. This is not optimal because, in many situations, the axis that is optimal for the fixation member does not reflect the best placement of the implant. Accordingly, there is a need for bone preparation systems and methods that provide greater flexibility as well as safety, reliability, and ease of use.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to facilitate secure attachment of an implant to bone. The present invention may have particular applicability to the installation of spinal implants such as facet joint implants, but may be used in many different areas of orthopedics, particularly in instances where it is desirable to have a fixation member with an angle independent of the angle of the implant. The configuration and operation of at least one embodiment of the invention will be shown and described in greater detail with reference to FIGS. 1 through 7, as follows.

Figure 1:
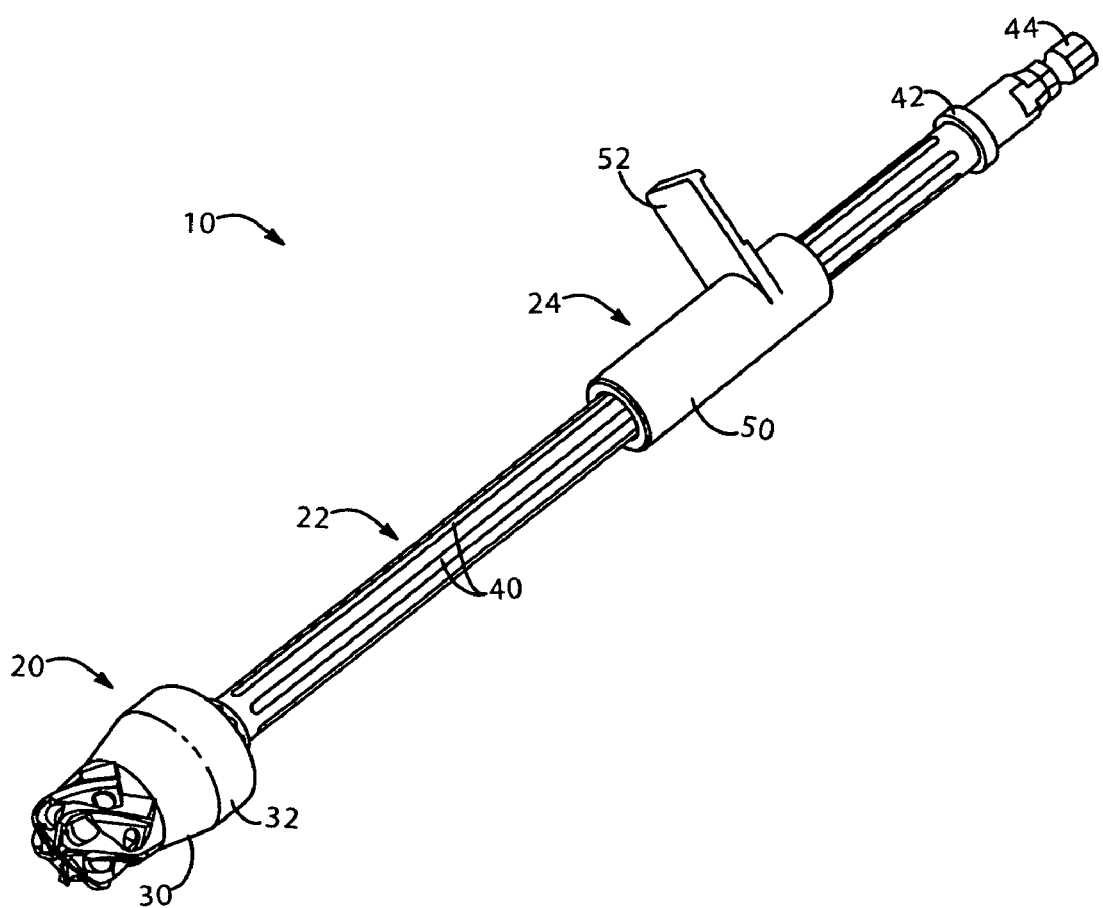
FIG. 1 is a perspective view of an apparatus according to one embodiment of the invention.

Referring to FIG. 1, a perspective view illustrates an apparatus 10 according to one embodiment of the invention. The apparatus 10 may be used to form a bone bed in a bone (not shown in FIG. 1), such as a saddle point of a vertebral pedicle, to facilitate attachment of an orthopedic implant to the bone. Thus, as embodied in FIG. 10, the apparatus 10 may be termed a "reamer," or reamer 10.

The reamer 10 may be used after insertion of a guide wire (not shown in FIG. 1) into the pedicle to form the bone bed around the guide wire entry point. The reamer 10 is designed to permit the bone bed to be formed at an angle that can vary substantially from the angle at which the guide wire enters the pedicle. The guide wire may subsequently be replaced with a fixation member (not shown in FIG. 1) such as a pedicle screw, which may be installed along the bore left by removal of the guide wire. Guidance of the reamer 10 by the guide wire ensures that the implant is appropriately positioned for retention by the fixation member.

The angle at which the implant is attached to the bone may be determined by the orientation of the bone bed. Accordingly, the reamer 10 may be used to permit the fixation member and the implant to be independently oriented with respect to the bone. This enables optimal orientation of the fixation member and the implant to ensure that the fixation member has optimal bone purchase to securely retain the implant, and the implant has the orientation needed to most effectively perform its function.

As shown in FIG. 1, the reamer 10 has a head 20 designed to ream the bone, a shank 22 attached to the head 20, and a collar 24 that encircles a portion of the shank 22. The head 20 may have a two-piece construction including a cutting component 30 at the distal end and a base component 32 secured to the shank 22.

The shank 22 may have a splined cross sectional shape with a plurality of grooves 40 extending along its length. The grooves 40 may facilitate cleaning of the shank 22. The shank 22 has a stop 42 near the proximal end thereof to keep the collar 24 from sliding off of proximal end. The stop 42 may take the form of a disc-shaped flange or the like. Furthermore, the shank 22 has a torquing interface 44 shaped to receive torque from a driver (not shown) such as an electric motor. The torquing interface 44 may have a polygonal cross sectional shape such as the hexagonal shape illustrated in FIG. 1.

The reamer 10 includes a coupling member designed to couple the reamer 10 to a stationary object. In the embodiment of FIG. 1, the coupling member takes the form of the collar 24, which has a tubular body 50 and an attachment flange 52. The tubular body 50 has a bore sized to receive the shank 22 such that the shank 22 is able to slide along its axis within the tubular body 50. The attachment flange 52 may be used to attach the collar 24 to a registration interface secured to a stationary object such as the bone, a nearby bone, an operating table, or the like. Sliding of the shank 22 within the tubular body 50 permits the head 20 to be advanced along the axis of the reamer 10 toward the site to be reamed.

According to one embodiment, the attachment flange 52 is coupled to a framework (not shown in FIG. 1) attached to the pedicles of a vertebra adjacent to the vertebra to be reamed. Such an embodiment may be particularly useful where the reamer 10 is to be used to ream a vertebra to prepare the vertebra to receive an implant that replaces one or more articular surfaces of the vertebra. For example, the framework may be attached to the L4 vertebra of a spine, and the reamer 10 may be coupled to the framework via the attachment flange 52 to guide the reamer 10 to ream a saddle point of a pedicle of the adjacent L5 vertebra. Such external attachment of a reamer according to the invention will be shown and described in greater detail in connection with FIG. 7.

Figure 2:
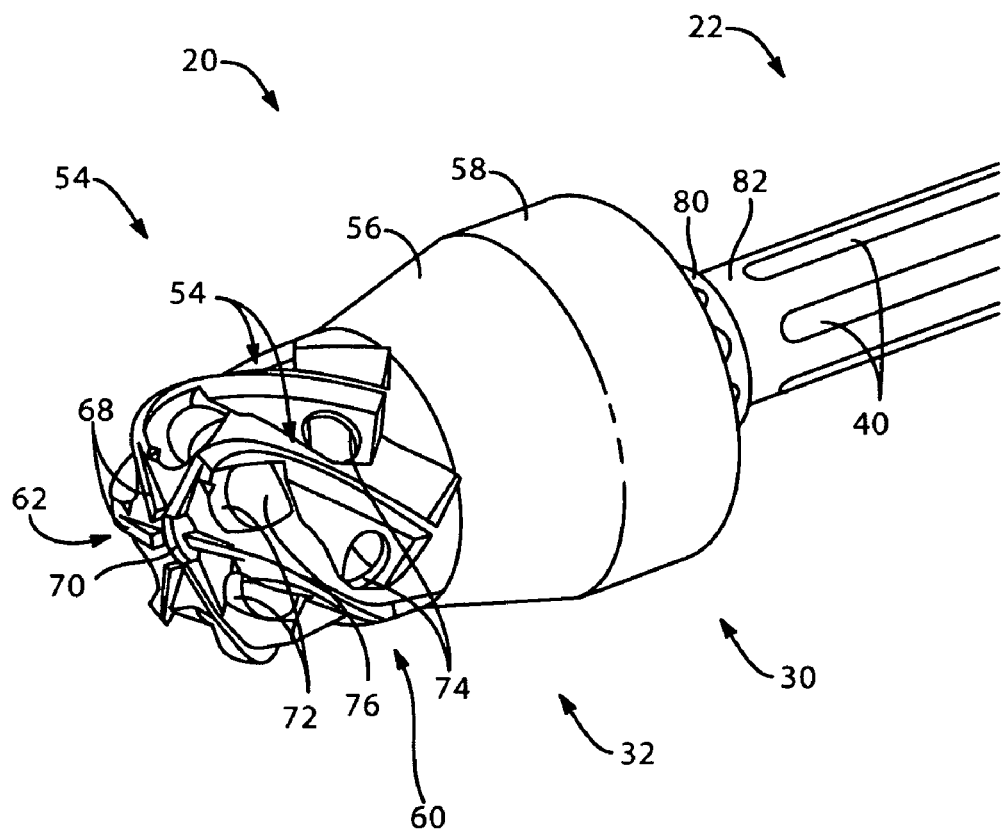
FIG. 2 is an enlarged, perspective view of the head of the apparatus of FIG. 1.

Referring to FIG. 2, an enlarged view illustrates the head 20 and the adjoining portion of the shank 22 of the reamer 10. As shown, the head 20 has a blade portion 54 at the distal end of the head 20, a frustoconical portion 56 adjacent to the blade portion 54, and an enlarged portion 58 at the proximal end of the head 20, adjacent to the frustoconical portion 56. The blade portion 54 has a side cutting surface 60, or side 60, with a generally cylindrical shape, and an end cutting surface 62, or end 62, with a generally circular shape, so that the blade portion 54, as a whole, is generally cylindrical.

The blade portion 54 has a plurality of blades 64 distributed in a radially symmetrical manner about the axis of the blade portion 54. Each of the blades 64 has a side portion 66 extending along the side 60 of the blade portion 54, and an end portion 68 extending along the end 62. The end portions 68 converge at a guide aperture 70 formed in the center of the end 62. The guide aperture 70 is sized to fit around the guide wire so that the exposed portion of the implanted guide wire can be inserted into the interior of the head 20. Thus, the head 20 is registered on the guide wire via engagement of the guide aperture 70 with the guide wire.

Figure 3:
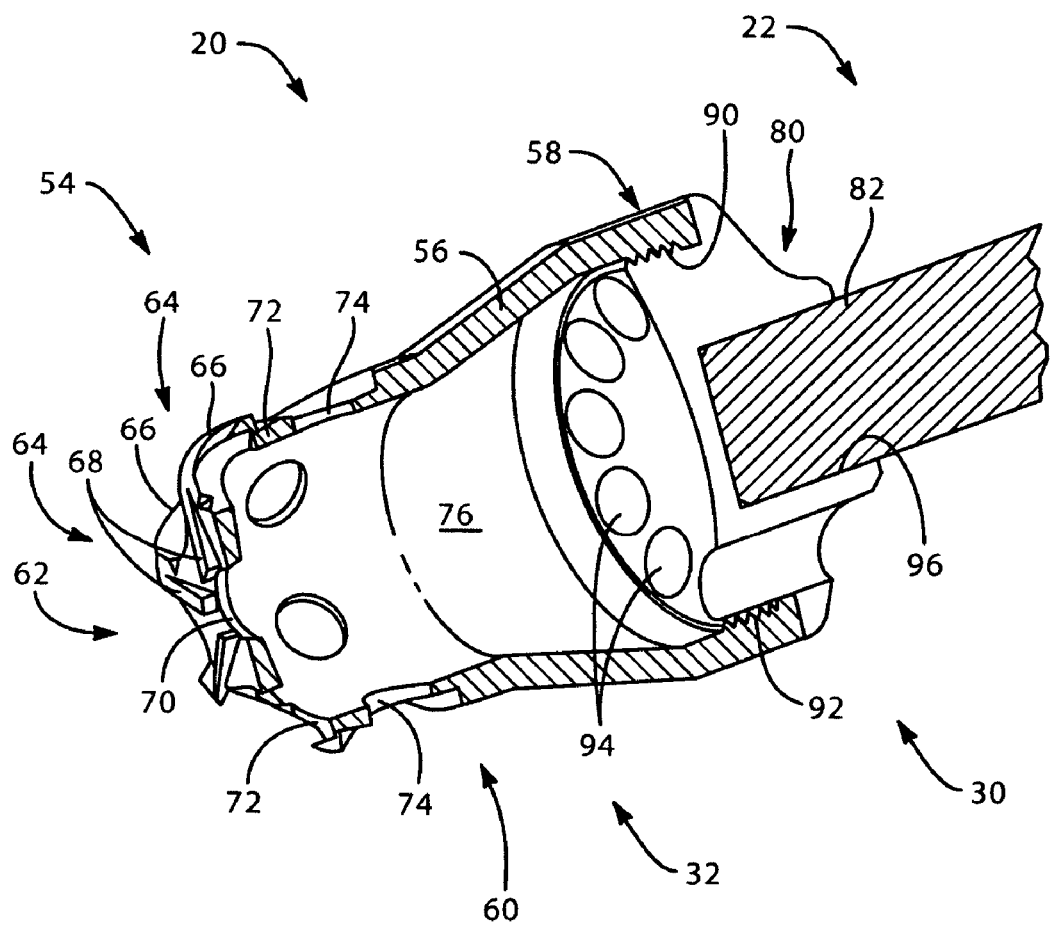
FIG. 3 is an enlarged, perspective section view of the head of the apparatus of FIG. 1.

In addition to the guide aperture 70, the blade portion 54 also has a plurality of terminal apertures 72 and a plurality of side apertures 74. The terminal apertures 72 and the side apertures 74 may be arranged in radially symmetrical fashion about the axis of the head 20 such that there is a terminal aperture 72 and a side aperture 74 positioned between each adjacent pair of blades 64. The terminal apertures 72 are positioned at the junction between the side 60 and the end 62. The side apertures 74 are positioned on the side 62. The apertures 72, 74 are in communication with a cavity 76 within the head 20. In the embodiment of FIGS. 1-3, the boundaries of the cavity 76 serve as a guide member interface by engaging the protruding portion of a guide wire or other guide member implanted in a bone, such as a vertebra.

The terminal apertures 72 and the side apertures 74 may perform a number of functions. The apertures 72, 74 may facilitate cleaning of the head 20 to remove material from within the cavity 76 after usage of the reamer 10. The apertures 72, 74 make the head 20 easier to position and use because they decrease the weight that must be supported by the surgeon and/or the associated frame (not shown in FIG. 2).

Furthermore, the apertures 72, 74, and more particularly the side apertures 74, may facilitate removal of the cutting component 30 from the base component 32 because a shaft (such as a guide wire) can easily be inserted through opposing side apertures 74. Such a shaft can then be rotated while holding the shank 22 stationary to remove the cutting component 30, thereby permitting easier access to the cavity 76 for cleaning.

The apertures 72, 74, and more particularly the terminal apertures 72, may facilitate manufacture of the head 20 by providing a relief behind the blades 64. Since the cutting component 30 may easily be manufactured with a five axis mill without the terminal apertures 72, the terminal apertures 72 are optional.

As shown, the base component 32 has a shank coupling portion 80. A coupling end 82 of the shank 22 is secured to the coupling portion 80. The manner in which the cutting component 30 is secured to the base component 32, and the manner in which the coupling end 82 is secured to the shank coupling portion 80, will be shown and described in greater detail in connection with FIG. 3.

Referring to FIG. 3, an enlarged, perspective section view illustrates the head 20 and the adjoining portion of the shank 22 of the reamer 10 of FIG. 1. As shown, the enlarged portion 58 of the cutting component 30 has threads 90 that extend generally inward. The threads 90 engage corresponding, outwardly-oriented threads 92 of the base component 32. The threads 90, 92 may engage each other in a direction such that, in response to rotation of the head 20 to ream the reaming site, the engagement of the threads 90, 92 is not loosened, but is instead tightened.

The base component 32 also has a plurality of apertures 94 arranged in a radially symmetrical manner about the axis of the reamer 10. Like the apertures 72, 74, the apertures 94 serve to make the head 20 lighter, and also facilitate cleaning of the head 20 to remove material from within the cavity 76. The apertures 94 generally encircle a shank coupling interface 96, which may take the form of a generally cylindrical recess within which the coupling end 82 of the shank 22 is retained. According to one example, the coupling end 82 is interference fitted into the shank coupling interface 96 for permanent attachment.

The blade portion 54, frustoconical portion 56, and enlarged portion 58 of the cutting component 30 provide the cavity 76 with a shape that enables the reamer 10 to vary considerably in orientation from the axis of the guide wire. More precisely, the flared shape of the frustoconical portion 56 and the enlarged diameter of the enlarged portion 58 provide an enlarged space toward the proximal portion of the head 20 to receive the exposed proximal end of the guide wire. The surfaces that bound the cavity 76, along both the distal and proximal portions, rotate along circular pathways sufficiently large to enable the axis of the head 20 to have a considerable angular offset from that of the guide wire. According to some examples, the axes of the head 20 and the guide wire may be offset from each other by fifteen degrees or more.

This angular offset is beneficial because the guide wire can be inserted at the proper angle for optimal bone purchase and patient safety, for example, along a pedicle axis. The implant may be oriented independently of the angle of the guide wire, and through the use of a polyaxial coupling or the like, may still be secured to a pedicle screw placed along the axis of the guide wire. Accordingly, if the implant is a facet joint replacement implant, the implant may be oriented for optimal articulation with an adjacent implant or natural articular surface.

According to one method of using the reamer 10 to form a bone bed in an L5 vertebra to receive a facet joint replacement implant, a framework may first be attached to the L4 vertebra, for example, by securing the framework to the pedicles of the L4 vertebra. The guide wire may then be implanted in the bone along the desired angle, either through the use of the framework, or independently. As mentioned previously, this angle may be selected for optimal purchase and safety of the fixation member that will subsequently be implanted in its place. The attachment flange 52 of the reamer 10 may then be secured to the framework, with the head 20 retracted to a position proximate the collar 24.

If desired, the framework may operate in such a manner that the orientation of the reamer 10 is fixed, but the reamer 10 is able to translate relatively freely to enable alignment of the head 20 with the guide wire. Alternatively, the framework may be selectively lockable, and may remain unlocked until the head 20 engages the guide wire. The framework may then be locked to control the orientation and/or position of the head 20.

The head 20 may then be advanced toward the guide wire by sliding the shank 22 through the collar 24 to permit motion of the head 20 away from the collar 24. The exposed proximal end of the guide wire is then inserted into the guide aperture 70 of the head 20. The torquing interface 44 of the shank 22 is coupled to a driver such as an electric motor, and the head 20 is rotated by the driver and further advanced toward the bone. As the head 20 is advanced, the rotating head 20 impinges against the bone, and the blades 64 cut away bone material to form the bone bed.

In formation of the bone bed, advancement of the head 20 may be guided by engagement of the guide wire and the guide aperture 70. Such guidance may ensure that the guide wire, and therefore the subsequently implanted fixation member, extends substantially through the center of the bone bed, and thus, through the center of the mounting interface of the corresponding implant.

After formation of the bone bed, the head 20 is retracted and the reamer 10 is removed from the framework. The guide wire is removed from the pedicle, and the fixation member is implanted in its place. The mounting interface of the implant is inserted into the bone bed such that the exposed proximal end of the fixation member extends through the mounting interface. The implant is oriented as desired with respect to the bone, and a fastening element such as a castle nut or a polyaxial fastening apparatus is coupled to the fixation member to keep the implant in place at the desired orientation.

The foregoing is only one example of a method of using the reamer 10. Those of skill in the art will recognize that other methods could be applied with the reamer 10, or with different reaming devices within the scope of the invention. According to certain alternative embodiments, it may be desirable to provide an offset between the axis about which reaming occurs and the axis along which torque is received. Such an arrangement may facilitate the use of a smaller incision, as will be described in connection with FIGS. 4 through 7.

Figure 4:
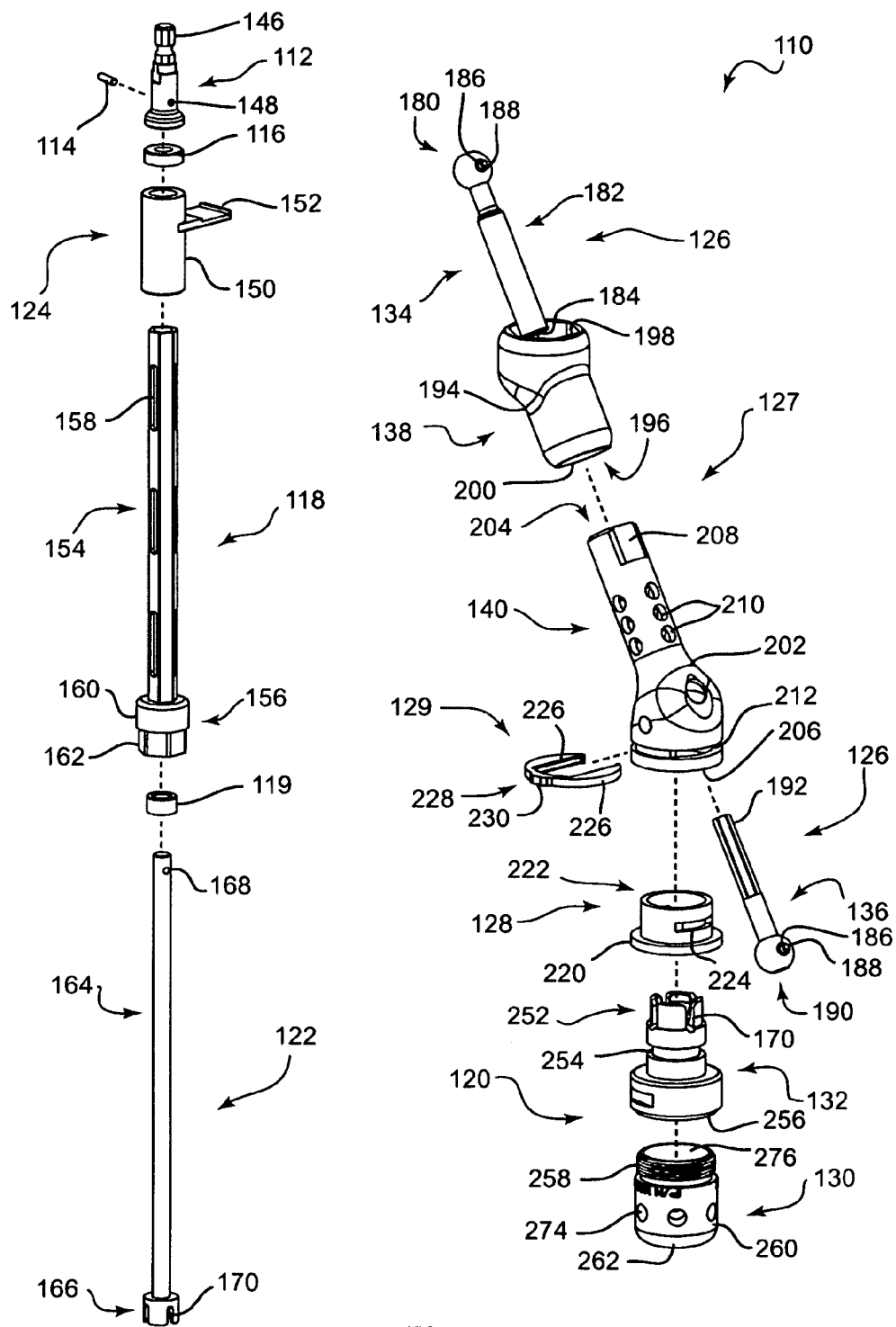
FIG. 4 is an exploded, perspective view of an apparatus according to another embodiment of the invention.

Referring to FIG. 4, an exploded, perspective view illustrates an apparatus according to another embodiment of the invention. The apparatus of FIG. 4 takes the form of a reamer 110. The reamer 110 is designed to provide an offset axis for transmission of torque to the reaming surface to facilitate reaming with a smaller incision, particularly in spinal applications such as pedicle reaming.

As shown, the reamer 110 has a torque receiver 112, a pin 114, a cap 116, a sleeve 118, a bushing 119, a reaming head 120 or head 120, a shank 122, a collar 124, an offset shaft 126, an offset sleeve 127, a cap 128, and a locking insert 129. The head 120 includes a cutting component 130 and a base component 132. The offset shaft 126 includes a proximal component 134 and a distal component 136. The offset sleeve 127 includes a proximal component 138 and a distal component 140. The configuration and operation of these various components will be set forth, as follows.

The torque receiver 112 is designed to be attached to a driver, such as an electric motor, to receive the torque that will ultimately drive rotation of the head 120. Accordingly, the torque receiver has a torquing interface 146 similar in shape to the torquing interface 44 of the shank 22 of the reamer 10. The torque receiver 112 also has a hole 148 passing transverse to its axis to facilitate attachment of the shank 122 to the torque receiver via the pin 114. The hole 148 passes through a cavity (not visible in FIG. 4) shaped to receive the end of the shank 122.

As in the previous embodiment, the collar 124 serves as a coupling member designed to couple the apparatus 110 to a stationary object such as the frame that will be shown and described in connection with FIG. 7. As in the previous embodiment, the collar 124 includes a tubular body 150 and an attachment flange 152 extending from the tubular body 150 for attachment to a corresponding registration interface on the frame.

The sleeve 118 has a generally tubular shape with a bore sized to receive the shank 122. The sleeve 118 is designed to slide within the collar 124 to permit advancement of the head 120 toward the surface to be reamed. Accordingly, the sleeve 118 may have an elongated portion 154 with a substantially polygonal cross section capable of sliding within the tubular body 150. The tubular body 150 may have bore with a corresponding polygonal shape. The polygonal shapes of the exterior surface of the elongated portion 154 and the bore of the tubular body 150 prevent the sleeve 118 from rotating with the shank 122. The sleeve 118 also has a stop portion 156 that is enlarged relative to the elongated portion 154.

As shown, the elongated portion 154 has a plurality of slots 158 extending along its length to provide access to the interior of the elongated portion 154. The slots 158 facilitate cleaning and/or lubrication of the bore of the elongated portion 154. The proximal end of the elongated portion 154 may be attachable to the cap 116, for example, by press fitting the proximal end into a recess (not shown in FIG. 4) formed on the distal end of the cap 116. The proximal surface of the cap 116 may form a bearing surface against which the distal surface of the torque receiver 112 rotates.

The stop portion 156 has a shoulder 160 that provides a lower limit to motion of the elongated portion 154 within the bore of the tubular body 150. Additionally, the stop portion 156 has an offset sleeve interface 162 that facilitates attachment of the proximal component 138 of the offset sleeve 127 to the sleeve 118. The offset sleeve interface 162 may have a polygonal exterior surface that mates with the proximal component 138 in a manner that prevents relative rotation between the sleeve 118 and the proximal component 138.

The shank 122 is designed to be rigidly coupled to the torque receiver 112 so that the shank 122 rotates within the sleeve 118. The shank 122 has an elongated portion 164 and an offset shaft interface 166. The elongated portion 164 is sized to fit within the bore of the elongated portion 154 of the sleeve 118 with sufficient clearance to permit relative rotation between the shank 122 and the sleeve 118. The elongated portion 164 has a hole 168 oriented transversely with respect to the axis of the shank 122 to receive the pin 114. More precisely, the pin 114 is inserted through the hole 148 of the torque receiver 112 and the hole 168 of the elongated portion 164 to rigidly couple the shank 122 to the torque receiver 112.

The offset shaft interface 166 transmits torque from the shank 122 to the proximal component 134 of the offset shaft 126 without any rigid coupling between the shank 122 and the proximal component 134. The offset shaft interface 166 has a generally crenellated shape having a plurality of slots 170 that interface with the proximal component 134 in a manner that will be shown and described in connection with FIG. 6.

As illustrated in FIG. 4, the proximal component 134 has a spherical end 180, an enlarged portion 182, and a bore 184 extending through at least a portion of the enlarged portion 182. The spherical end 180 is sized to fit into a cavity defined by the crenellated shape of the offset shaft interface 166. The spherical end 180 has a hole 186 extending transverse to the axis of the proximal component 134. A post 188 is positioned in the hole 186 such that the ends of the post 188 protrude from both sides of the spherical end 180. The post 188 may be rigidly attached to the spherical end 180, and may optionally be permanently attached via press fitting, welding, or the like.

The distal component 136 of the offset shaft 126 has a spherical end 190 and a proximal end 192. The spherical end 190 may be substantially identical to the spherical end 180 of the proximal component 134, and may thus have a hole 186 with a post 188 positioned therein. The proximal end 192 is sized to fit into the bore 184 of the proximal component 134 so that the proximal and distal components 134, 136 may be assembled together to form the offset shaft 126. The proximal end 192 and the bore 184 may have corresponding polygonal cross sectional shapes, or other non-circular cross sectional shapes that prevent relative rotation between the proximal and distal components 134, 136 when they are assembled together.

The proximal component 138 of the offset sleeve 126 may have an elbow 194 and a bore 196 extending between proximal and distal ends of the proximal component 138. The elbow 194 provides an angular offset between the proximal and distal ends, thereby causing the offset shaft 126 to be nonparallel to the shank 122. The bore 196 of the proximal component 138 has a sleeve receiver 198 and a distal component interface 200. The sleeve receiver 198 may have a polygonal cross sectional shape that corresponds to the polygonal shape of the offset sleeve interface 162 of the stop portion 156 of the sleeve 118. The offset sleeve interface 162 can thus be received within the sleeve receiver 198 such that relative rotation between the proximal component 138 and the sleeve 118 cannot occur. If desired, the offset sleeve interface 162 and the stop portion 156 may fit together with a slight interference so that they can be assembled or disassembled by hand, but will otherwise remain attached together during use.

At the distal end of the proximal component 138, the bore 196 has a distal component interface 200 designed to receive the distal component 140 in a manner that prevents relative rotation between the proximal and distal components 138, 140. The distal component interface 200 may have a generally circular shape with one straight segment.

The distal component 140 of the offset sleeve 126 may have an elbow 202 and a bore 204 extending between proximal and distal ends of the distal component 140. The elbow 202 provides an angular offset between the proximal and distal ends, thereby causing the head 120 to be nonparallel to the offset shaft 126. The bore 204 of the distal component 140 has a cap receiver 206 shaped to receive the cap 128. The proximal end of the distal component 140 has a proximal component interface, which may take the form of a flat 208 formed on the exterior surface of the proximal end to mate with the distal component interface 200 of the bore 184 of the proximal component 138.

Additionally, the distal component 140 has a plurality of ports 210 that provide access to the bore 204, and a pair of distal slots 212. The ports 210 may facilitate cleaning and/or lubrication of the bore 204. The distal slots 212 receive the locking insert 129 in a manner that permits rotation of the base component 132 of the head 120 within the cap 128, as will be shown and described in greater detail subsequently.

As illustrated in FIG. 4, the cap 128 may have a shoulder 220 positioned to abut the base component 132 of the head 120, and a tubular portion 222 insertable into the cap receiver 206 of the distal component 140. The tubular portion 222 has a pair of slots 224 that align with the distal slots 212 of the distal component 140 when the tubular portion 222 is inserted into the cap receiver 206. The slots 224 cooperate with the distal slots 212 to receive the locking insert 129.

The locking insert 129 has a pair of arms 226 that are bounded by a generally circular shape, but have flat inwardly oriented surfaces. The arms 226 are coupled together by a bridge 228 at one end of the locking insert 129. The bridge 228 has a tab 230 that protrudes to facilitate gripping, insertion, and removal of the locking insert 129. The arms 226 slide into the slots 224 and the distal slots 212 along a direction generally parallel to the slots 224. When the arms 226 are in position within the slots 224 and the distal slots 212, the bridge 228 abuts the portion of the distal component 140 between the distal slots 212. The flat, inwardly oriented surfaces of the arms 226 extend into the bore 204 of the distal component 140.

The base component 132 of the head 120 has an offset shaft interface 252, an annular groove 254, and a cutting component interface 256. The offset shaft interface 252 receives torque from the offset shaft 126 without any rigid coupling between the offset shaft 126 and the base component 132. The offset shaft interface 252 may be substantially identical to the offset shaft interface 166 of the shank 122, and may thus have a crenellated shape with slots 170 designed to receive the protruding ends of the post 188 of the distal end of the offset shaft 126. Thus, rotation of the post 188 causes rotation of the offset shaft interface 252 about an axis angularly offset from that of the offset shaft 126.

The annular groove 254 is positioned to align with the slots 224 and the distal slots 212 when the cap 128 is positioned in the cap receiver 206 of the distal component 140 and the proximal portion of the base component 132 is positioned within the tubular portion 222 of the cap 128. Upon insertion of the arms 226 of the locking insert 129 into the slots 224 and the distal slots 212, the flat, inwardly oriented surfaces of the arms 226 slide into the annular groove 254. Within the annular groove 254, the arms 226 do not impede rotation of the base component 132, but they block withdrawal of the proximal portion of the base component 132 from within the cap 128 and the cap receiver 206 of the distal component 140.

The cutting component interface 256 facilitates attachment of the cutting component 130 to the base component 132. The cutting component interface 256 may take the form of a plurality of inwardly oriented threads that engage corresponding threads of the cutting component 256.

As shown in FIG. 4, the cutting component 130 may have a base component interface 258, a side cutting surface 260, and an end cutting surface 262. The base component interface 258 may take the form of a plurality of outwardly oriented threads that engage the threads of the cutting component interface 256 of the base component 132. The threads may engage each other in such a way that, as reaming is carried out, the engagement of the threads is tightened, not loosened.

The side cutting surface 260 and the end cutting surface 262 may be configured similarly to the side cutting surface 60 and the end cutting surface 62 of the previous embodiment, and may thus have blades (not shown in FIG. 4) like the blades 64 shown in FIG. 2. Alternatively, the cutting surfaces 260, 262 of the cutting component 130 may have other cutting features (not shown) such as abrasive texturing, ridges, grooves, and the like.

The side cutting surface 260 may have a plurality of side apertures 274 that provide access to a guide member interface within the interior of the head 120. In the embodiment of FIG. 4, the guide member interface comprises the surface bounding a cavity 276 within the head 120. The cavity 276 has a generally conical shape, as will be shown and described in connection with FIG. 6. A guide aperture (not visible in FIG. 4) like the guide aperture 70 of the previous embodiment is present in the end cutting surface 262.

The reamer 110 may be assembled according to a variety of different methods. According to one method, the elongated portion of the sleeve 118 is first inserted into the bore of the tubular body 150 of the collar 124. The cap 116 is then attached to the proximal end of the elongated portion. Then, the elongated portion 164 of the shank 122 is inserted through the bushing 119 until the bushing 119 rests against the offset shaft interface 166 of the shank 122.

The proximal end of the elongated portion 164 of the shank 122 is inserted through the bore of the sleeve 118 until it emerges from the proximal end of the sleeve 18 and the bushing 119 slides into a corresponding recess formed in the stop portion 156 of the sleeve 118. The proximal end of the elongated portion 164 is then inserted into the corresponding recess in the distal end of the torque receiver, and the pin 114 is inserted through the hole 148 of the torque receiver and the hole 168 of the elongated portion 164 to secure the torque receiver 112 to the elongated portion 164.

Next, the proximal component 138 and the distal component 140 may be assembled to form the offset sleeve 127. More precisely, the proximal end of the distal component 140 may be inserted into the distal component interface 200 such that the flat 208 is aligned with a corresponding flat (not shown) of the distal component interface 200. Press fitting or other methods may be used to keep the components 138, 140 together.

After the posts 188 have been inserted into the holes 186 and secured therein, the offset shaft 126 may be formed by securing the proximal component 134 to the distal component 136. More precisely, the mating ends of the proximal and distal components 134, 136 are inserted into the assembled offset sleeve 127 as shown in FIG. 4, and then the proximal end 192 of the distal component 136 is inserted into the bore 184 of the proximal component 134 and retained therein via press fitting or the like.

After assembly of the offset shaft 126 and the offset sleeve 127, the stop portion 156 of the sleeve 118 is attached to the proximal component 138 of the offset sleeve 127. More precisely, the protruding ends of the post 188 of the spherical end 180 are aligned with the slots 170 of the offset shaft interface 166, and the spherical end 180 is inserted into the offset shaft interface 166 such that the ends of the post 188 engage the slots 170. Simultaneously, the offset sleeve interface 162 is inserted into the sleeve receiver 198 of the proximal component 138 of the offset sleeve 127. A press fit or some other mechanism may optionally be used to retain the sleeve interface 162 within the sleeve receiver 198.

As result of performance of the foregoing steps, the offset sleeve 127 is secured to the sleeve 118, and the offset shaft 126 is coupled to the shank 122 such that torque may be transmitted therebetween. The cap 128 is then coupled to the distal end of the distal component 140 of the offset sleeve 127. This is carried out by inserting the tubular portion 222 of the cap 128 into the cap receiver 206 of the distal component 140 such that the slots 224 of the tubular portion 222 align with the distal slots 212 of the distal component 140. A press fit or other mechanism may be used to keep the tubular portion 222 in place within the cap receiver 206.

The head 120 may then be assembled by attaching the cutting component 130 to the base component 132. For example, the threads of the cutting component interface 256 may be rotated into engagement with the threads of the base component interface 258. Then, the offset shaft interface 252 of the base component 132 may be inserted into the tubular portion 222 of the cap 128 until the exposed ends of the post 188 of the spherical end 190 of the distal component 190 of the offset shaft 126 slide into the slots 170 of the offset shaft interface 252.

The annular groove 254 of the base component 132 will then be aligned with the slots 224 of the cap 128 and the distal slots 212 of the distal component 140 of the offset sleeve 127. Therefore, the locking insert 129 can slide into engagement with the slots 224 and the distal slots 212 such that the inwardly oriented surfaces of the arms 226 are positioned within the annular groove 254 to prevent withdrawal of the proximal end of the base component 132 from the cap 128, as described previously.

Figure 5:
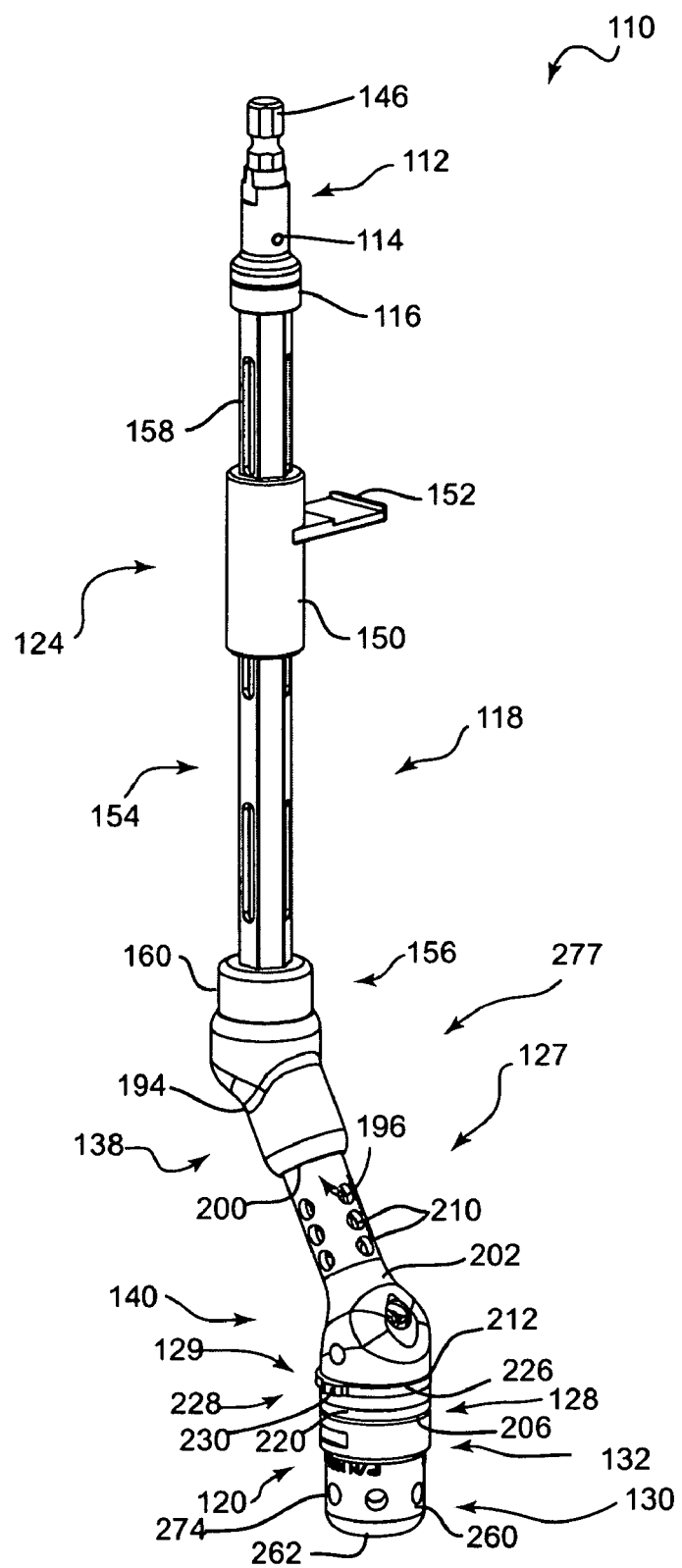
FIG. 5 is a perspective view of the apparatus of FIG. 4 in a fully assembled state.

Referring to FIG. 5, a perspective view illustrates the reamer 110 in fully assembled form, after performance of the steps outlined previously. The reamer 110 is now ready for use. As shown, the offset shaft 126, offset sleeve 127, and associated portions of the surrounding parts define an offset assembly 277 that offsets the head 120 from the torque receiver 112. This offset facilitates the use of a smaller incision to carry out the reaming and implantation procedures, as will be described subsequently.

Figure 6:
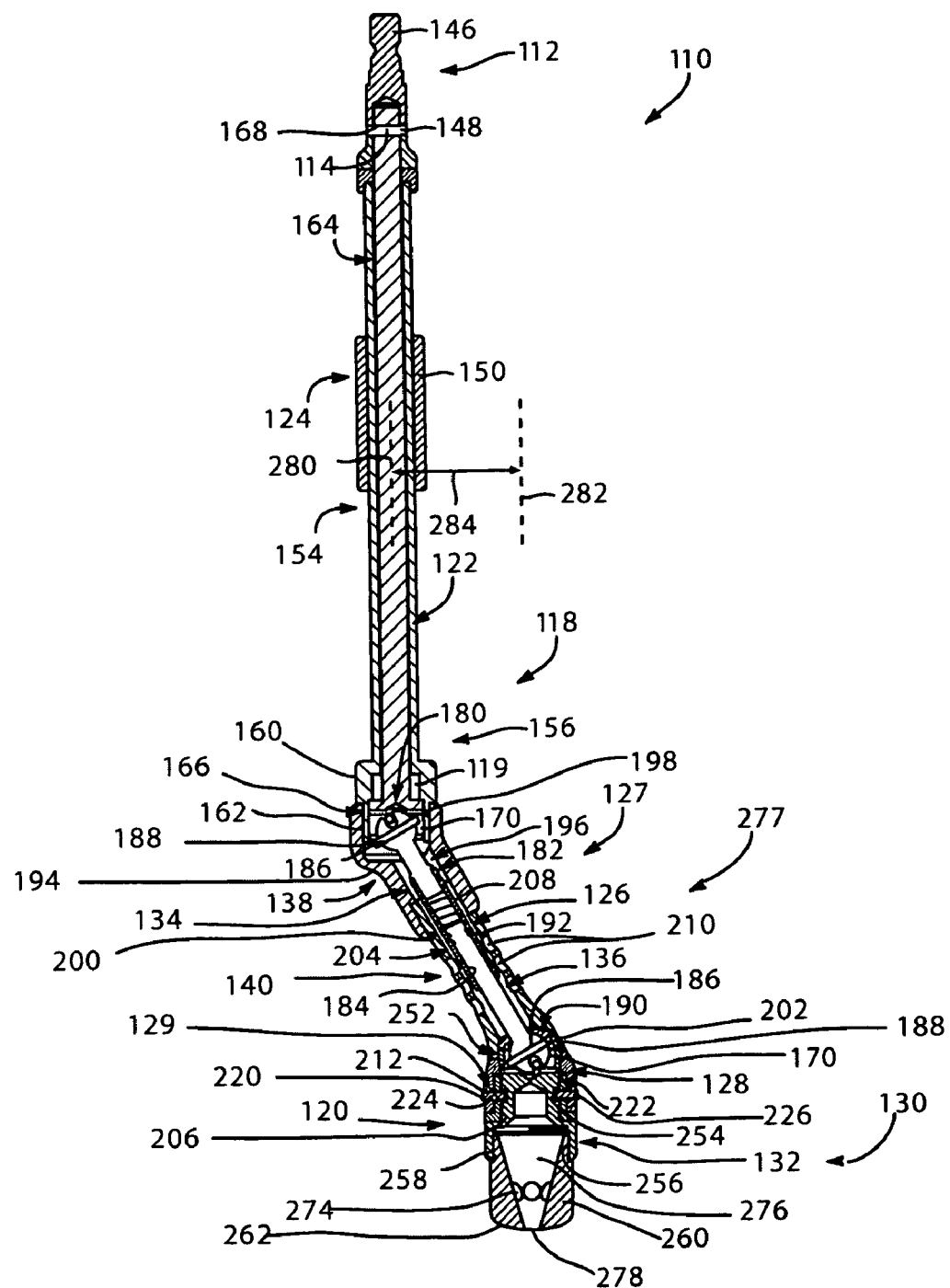
FIG. 6 is a side elevation, section view of the apparatus of FIG. 4 in the fully assembled state.

Referring to FIG. 6, a side elevation, section view illustrates the reamer 110 in the fully assembled state. The manner in which the various components of the reamer 110 fit together is more clearly shown.

Additionally, FIG. 6 illustrates the presence of a guide aperture 278 in the end cutting surface 262. The shape of the cavity 276 is also more clearly illustrated; as shown in FIG. 6, the cavity 276 may have a conical shape with a diameter that matches that of the guide aperture 278 at the distal end of the head 120, and flares to a larger diameter proximally. The cavity 276 thus has a shape that enables the head 120 to rotate around a guide wire (not shown in FIG. 6) extending into the cavity 276 at any of a plurality of relative orientations between the head 120 and the guide wire.

As also shown in FIG. 6, the shank 122 and the torque receiver 112 have a first axis of rotation 280. The head 120 has a second axis of rotation 282. The offset assembly 277 provides an offset 284 between the first and second axes of rotation 280, 282. Those of skill in the art will recognize that a wide variety of alternative offset assemblies (not shown) may be used to carry out a similar function. Such alternative offset assemblies may use meshing gears, chain drives, belt drives, frictional couplings, or the like to provide such an offset between axes of rotation.

Figure 7:
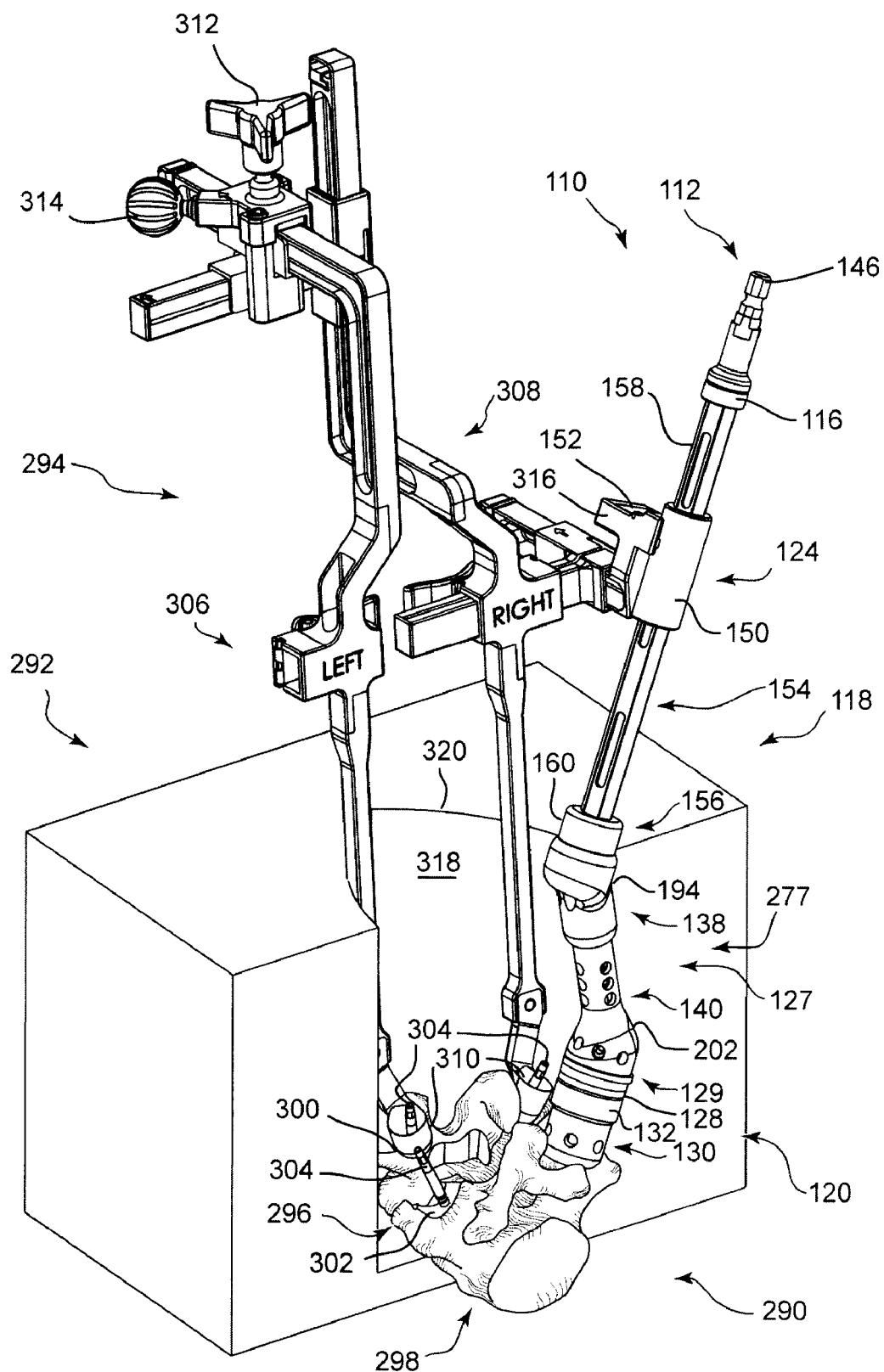
FIG. 7 is a perspective view of the apparatus of FIG. 4 secured to a frame to ream a pedicle of a vertebra, with a block illustrated to represent soft tissues surrounding the operating site.

Referring to FIG. 7, a perspective view illustrates the reamer 110 in position to resect a portion of a spine 290. A block 292 is also shown surrounding a portion of the spine 290 to represent surrounding tissue. Further, a frame 294 is shown attached to the spine 290 and to the reamer 110 to stabilize the reaming operation.

The illustrated portion of the spine 290 includes a superior vertebra 296 and an inferior vertebra 298. The superior vertebra 296 has two pedicles with saddle points 300 that may be used to attach one bilateral implant, or two separate unilateral implants, to the superior vertebra 296. According to one example, the superior vertebra 296 is to receive two inferior facet joint replacement prostheses (not shown), which are to be attached to the saddle points 300. Similarly, the inferior vertebra 298 has two pedicles with saddle points 302 that may be used to attach one bilateral implant, or two separate unilateral implants, to the inferior vertebra 298. The reamer 110 may, for example, be used to ream the saddle points 302 of the inferior vertebra 298 to receive two superior facet joint replacement prostheses (not shown).

As shown, a plurality of guide members in the form of guide wires 304 have been implanted in the saddle points 300, 302 of the vertebrae 296, 298. The guide wires 304 are implanted through the use of methods known to spinal orthopedic surgeons, and need not be implanted at specific angles relative to the vertebrae 296, 298. The guide wires 304 are to be removed prior to implantation of fixation members, such as pedicle screws, which will be used to anchor the facet joint replacement prostheses to the vertebrae 296, 298.

As shown, the frame 294 has a left arm 306 and a right arm 308. Each of the arms 306, 308 has an anchor 310 at the distal end. The anchors 310 rest on the saddle points 300 of the superior vertebra 296, which may have been previously reamed or otherwise resected to prepare them to receive the anchors 310. Each of the anchors 310 may have an aperture (not shown) that receives the corresponding previously implanted guide wire 304. Thus, the anchors 310 serve to provide registration of the frame 294 to known points on the superior vertebra 296.

The anchors 310 of the frame 294 may be independently positionable. Accordingly, a locking mechanism 312 may be used to permit relative motion of the arms 306, 308, and locking of the relative positions of the arms 306, 308 when the anchors 310 are properly positioned. The frame 294 also has an external anchoring feature 314 that permits attachment of the frame 294 to a stationary reference such as an operating table or the like. A separate adjustably lockable anchoring arm (not shown) may be used to secure the external anchoring feature 314 to the stationary reference.

The frame 294 also has a registration interface 316 to which the reamer 310 may be attached. More precisely, the registration interface 316 may include a bore (not shown) that receives the attachment flange 152 of the collar 124. A lever or some other locking mechanism may be used to lock the attachment flange 152 in place within the bore. If desired, the registration interface 316 may be adjustably positionable with respect to the remainder of the frame 294 to compensate for variations in spinal anatomy. In any case, the registration interface 316 holds the collar 124 stationary with respect to the inferior vertebra 298 so that the head 120 can be advanced along a known trajectory to ream the corresponding saddle point 302.

According to one method of preparing the spine 290 to receive the implants, the operating area may first be prepared by forming an access port 318 in the block 292 to provide access to the portion of the spine 290. The access port 318 includes an incision 320 made on the surface of the skin, represented by the corresponding surface of the block 292.

The guide wires 304 may then be implanted in the pedicles of the vertebrae 296, 298 through the use of known methods. The saddle points 300 of the superior vertebra 296 may then be reamed to provide substantially semispherical surfaces that can receive the corresponding surfaces of the anchors 310 at multiple relative orientations. The frame 294 may then be placed on the saddle points 300 and aligned with the sagittal plane of the spine 290. Once the frame 294 has been properly aligned, the external anchoring feature 314 may be secured to the external reference to prevent relative motion between the frame 294 and the spine 290.

The protruding portion of the guide wire 304 in the saddle point 302 to be reamed may then be inserted into the guide aperture 278 of the head 120 of the reamer 110. The head 120 may be advanced along the protruding portion of the guide wire 304 until it is proximate the bone surface to be reamed. Then, the attachment flange 152 may be attached to the registration interface 316 of the frame 294 to control the angle at which the saddle point 302 is reamed. The torque receiver 112 of the reamer 110 may then be coupled to a driver (not shown) and rotated to cause rotation of the head 120. The rotation of the head 120 removes material from the saddle point 302 to the desired depth.

In the illustration of FIG. 7, the other (left) saddle point 302 of the inferior vertebra 298 has already been reamed through the use of a procedure like that described above. Further resection operations may be performed as needed through the use of the frame 294, and the frame 294 may be removed. The guide wires 304 may be removed, and fixation members such as pedicle screws may be inserted into the pedicles of the vertebrae 296, 298 in their places. Implants may be placed on the saddle points 300, 302 and fixed in place via the fixation members. Guidance of the reaming operation with the guide wires 304 helps to ensure that the fixation members pass through the centers of the corresponding mounting interfaces of the implants.

The reamer 110 offers the benefits set forth in the description of the reamer 10 of the previous embodiment. More precisely, the guide wires 304 need not be implanted at specific angles to enable proper reaming to be carried out. Thus, the guide wires 304 can be implanted at angles that are optimal for placement of the fixation members, and the resection surfaces formed by the reaming operation will be oriented at angles that are independent of the angles of the guide wires 304. Thus, the saddle points 302 may be prepared to receive the superior facet joint prostheses at angles that are most beneficial to their operation, regardless of the angle at which the fixation members are implanted in the inferior vertebra 298.

The reamer 10 of the previous embodiment may be coupled to the frame 294 in a manner substantially the same as that set forth in the foregoing description, in connection with the reamer 110. However, the reamer 110 provides additional benefits because, through the use of the offset assembly 277, the reamer 110 may be usable to ream the saddle points 302 while keeping the incision 320 relatively small. With reference to FIG. 7, it can be envisioned that, without the offset assembly 277, the incision 320 might need to extend further laterally in both directions to accommodate the full length of the reamer. Thus, usage of the reamer 110 may facilitate the process of accessing the relevant portion of the spine 290, and may expedite healing of the wound site after the operation is completed.

The present invention may be embodied in other specific forms without departing from its spirit or essential characteristics. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for resecting a bone, the apparatus comprising:

a guide member for implantation in the bone at an implantation location and an implantation orientation, wherein the implantation orientation comprises any of a plurality of relative orientations between the guide member and the bone;

a guide member interface configured to engage the guide member, wherein the guide member interface encloses a conical space, wherein the guide member engages the guide member interface proximate the apex of the conical space; and a cutting surface positionable to resect the bone at a resection location determined by the implantation location of the guide member, wherein the resection location is substantially independent of the implantation orientation of the guide member.

2. The apparatus of claim 1, wherein the guide member interface is further configured to engage the guide member at an engagement orientation comprising any of a plurality of relative orientations between the guide member and the guide member interface, wherein the resection location is further substantially independent of the engagement orientation.

3. The apparatus of claim 2, wherein the guide member comprises a guide wire having an elongated shape.

4. The apparatus of claim 1, wherein the guide member interface comprises a cavity having a substantially conical shape with a narrow end and a wider end, the narrow end having a port through which a protruding portion of the guide member is insertable.

5. The apparatus of claim 1, wherein the cutting surface is incorporated into a reaming head, the apparatus further comprising a shaft configured to convey torque to the reaming head.

6. The apparatus of claim 5, further comprising a frame coupling member configured to removably couple the apparatus to a frame anchored in a substantially stationary manner with respect to the bone.

7. The apparatus of claim 6, wherein the frame coupling member comprises a sliding interface configured to permit translation of the reaming head toward the bone.

8. The apparatus of claim 5, wherein the shaft is configured to rotate about a first axis of rotation and the reaming head is configured to rotate about a second axis of rotation, the apparatus further comprising an offset assembly that transmits torque from the shaft to the reaming head such that the first and second axes of rotation are not coaxial.

9. An apparatus for resecting a bone, the apparatus comprising:

a guide member for implantation in the bone at an implantation location;

a shaft configured to receive torque; and a reaming head coupled to the shaft, the reaming head comprising:

a cavity that converges to a port sized to receive a protruding portion of the guide member, wherein the cavity is shaped to receive the protruding portion at an engagement orientation comprising any of a plurality of relative orientations between the guide member and the cavity, and a cutting surface shaped to resect the bone, wherein the cutting surface is positionable at a resection location in response to receipt of the protruding portion within the cavity, wherein the resection location is substantially independent of the engagement orientation.

10. The apparatus of claim 9, wherein the guide member comprises a guide wire having an elongated shape.

11. The apparatus of claim 10, wherein the cavity comprises a substantially conical shape with a narrow end and a wider end, the narrow end having the port through which the protruding portion is insertable.

12. The apparatus of claim 9, further comprising a frame coupling member configured to removably couple the apparatus to a frame anchored in a substantially stationary manner with respect to the bone.

13. The apparatus of claim 12, wherein the frame coupling member comprises a sliding interface configured to permit translation of the reaming head toward the bone.

14. The apparatus of claim 9, wherein the shaft is configured to rotate about a first axis of rotation and the reaming head is configured to rotate about a second axis of rotation, the apparatus further comprising an offset assembly that transmits torque from the shaft to the reaming head such that the first and second axes of rotation are not coaxial.

15. A method of resecting a bone, the method comprising:

implanting a guide member in the bone at an implantation location and an implantation orientation, wherein the implantation orientation comprises any of a plurality of relative orientations between the guide member and the bone;

engaging the guide member with a guide member interface that encloses a conical space, wherein the guide member engages the guide member interface proximate the apex of the conical space;

positioning a cutting surface proximate a resection location determined by the implantation location of the guide member, wherein the resection location is substantially independent of the implantation orientation of the guide member; and actuating the cutting surface to resect the bone at the resection location.

16. The method of claim 15, wherein engaging the guide member with the guide member interface comprises engaging the guide member at an engagement orientation comprising any of a plurality of relative orientations between the guide member and the guide member interface, wherein the resection location is further substantially independent of the engagement orientation.

17. The method of claim 16, wherein the guide member comprises a guide wire having an elongated shape, wherein the guide member interface comprises a cavity having a substantially conical shape with a narrow end and a wider end, wherein engaging the guide member comprises inserting a protruding portion of the guide wire through a port on the narrow end.

18. The method of claim 15, wherein the cutting surface is incorporated into a reaming head, wherein actuating the cutting surface comprises transmitting torque to the reaming head through a shaft.

19. The method of claim 18, further comprising:

removably coupling the reaming head to a frame anchored in a substantially stationary manner with respect to the bone through the use of a coupling member having a sliding interface; and actuating the sliding interface to translate the coupled reaming head toward the bone.

20. The method of claim 18, wherein actuating the cutting surface comprises:

rotating the shaft about a first axis of rotation;

transmitting torque from the shaft to the reaming head; and rotating the reaming head about a second axis of rotation in response to transmission of the torque to the reaming head, wherein the first and second axes of rotation are not coaxial.

* * * * *